United States Patent
Jarvis

(10) Patent No.: US 6,253,621 B1
(45) Date of Patent: Jul. 3, 2001

(54) MICRO-VOID DETECTION

(75) Inventor: Richard W. Jarvis, Austin, TX (US)

(73) Assignee: Advanced Micro Devices, Sunnyvale, CA (US)

( * ) Notice: Subject to any disclaimer, the term of this patent is extended or adjusted under 35 U.S.C. 154(b) by 0 days.

(21) Appl. No.: 09/387,182

(22) Filed: Aug. 31, 1999

(51) Int. Cl.⁷ .................................................... G01N 29/04
(52) U.S. Cl. ................................................................ 73/655
(58) Field of Search ............................... 73/643, 655, 657

(56) References Cited

U.S. PATENT DOCUMENTS

| | | | |
|---|---|---|---|
| 5,333,495 | * 8/1994 | Yamaguchi et al. | 73/105 |
| 5,457,997 | * 10/1995 | Naruo et al. | 73/643 |
| 5,600,133 | * 2/1997 | Spillman, Jr. | 250/227.14 |
| 5,608,526 | 3/1997 | Piwonka-Corle et al. . | |
| 5,633,747 | 5/1997 | Nikoonahad . | |
| 5,771,094 | 6/1998 | Carter et al. . | |
| 5,840,023 | 11/1998 | Oraevsky et al. . | |

OTHER PUBLICATIONS

A. Grossman et al., "A new millimeter free electron laser using a relativistic beam with spiraling electrons," Phys. Fluids 26(1), Jan. 1983, 1983 American Institute of Physics, pp. 337–343.

S.T. Zavtrak, "Free gas bubbles acoustic laser," The Institute of Nuclear Problems, Bobruiskaya Str., 11, Minsk 220050, Belarus, 1995 Elsevier Science B.V., A358(1995) pp. 473–474.

* cited by examiner

Primary Examiner—Richard A. Moller

(57) ABSTRACT

According to an example embodiment of the present invention, a semiconductor device having conductive structure is analyzed using acoustic energy. Acoustic energy is generated in the device, and a resulting acoustic wave is detected. Using the detected wave, an index of refraction of a portion of the conductive structure is determined as a function of the wave. The calculated index of refraction is used and at least one defect in the conductive structure is detected. Using this method, defects can be detected during or after the manufacture of semiconductor devices in a cost effective, reliable manner. This method is particularly useful for defects that are not detectable using typical optical scanning methods due to opaque material in semiconductor devices.

20 Claims, 3 Drawing Sheets

MICRO-VOID DETECTION

FIELD OF THE INVENTION

The present invention relates generally to semiconductor devices and their fabrication and, more particularly, to semiconductor devices and their manufacture involving analyzing the devices for defects.

BACKGROUND OF THE INVENTION

The semiconductor industry has recently experienced technological advances that have permitted dramatic increases in circuit density and complexity, and equally dramatic decreases in power consumption and package sizes. Present semiconductor technology now permits single-chip microprocessors with many millions of transistors operating at speeds of hundreds of millions of instructions per second to be packaged in relatively small, air-cooled semiconductor device packages. A by-product of such high-density and high functionality has been an increase in the number and complexity of the manufacturing processes, as well as an increase in the difficulties of maintaining satisfactory levels of quality control, analyzing the devices for defects, and providing a cost-effective product using such processes.

As the manufacturing processes for semiconductor devices and integrated circuits increase in difficulty, methods for testing and debugging these devices become increasingly important. Not only is it important to ensure that individual chips are functional, it is also important to ensure that batches of chips perform consistently. In addition, the ability to detect a defective manufacturing process early is helpful for reducing the number of defective devices manufactured, a cost avoidance methodology.

One type of defect that is prevalent in semiconductor device manufacture involves the generation of regions within metal structure of the device that lack sufficient metal, resulting in voids. Such voids are often created during canal (or trench) patterning, conductive film deposition, and canal and contact fill. The detection of voids is important because the circuit reliability depends upon having sufficient conductive material in these regions. One type of analysis that has been employed for defect detection is optical scanning. Optical scanning can be useful for analyzing patterns in the device. However, optical scanning is not as useful for analyzing shapes at the bottom of contacts and canals. In particular, when contact and canal fill includes opaque films like copper, metal below the films is not visible via optical scanning.

Some of the features of typical semiconductor device structures for which defect analysis is important include metal interconnects, devices, and other circuitry formed within the device. Many semiconductor devices now employ multiple circuit layers having multiple connections within each layer as well as between the layers. These additional layers hinder access to portions of the circuitry buried below or in between one or more of the layers. As the density of these layers and components increases, viewing and analyzing the structure for defects becomes more difficult, and in some cases, not possible. The difficulty, cost, and destructive aspects of existing methods for testing semiconductor devices for defects are impediments to the growth and improvement of semiconductor technologies.

SUMMARY OF THE INVENTION

The present invention is exemplified in a number of implementations and applications, some of which are summarized below. According to an example embodiment, the present invention is directed to a method for analyzing a semiconductor device having conductive structure. Acoustic energy is generated in the device, and a resulting acoustic wave is detected. An index of refraction of a portion of the conductive structure is calculated as a function of the wave, and used to detect at least one defect in the conductive structure. Using this method, semiconductor devices can be tested for defects in a relatively inexpensive and reliable manner.

According to another example embodiment of the present invention, a semiconductor device is manufactured. Conductive structure is formed within the device. Acoustic energy is generated in the device and a resulting acoustic wave is detected. An index of refraction of a portion of the conductive structure is calculated as a function of the wave and the existence of a defect in the device is determined. In response to detecting whether a defect exists in the device, the manufacture of the device is controlled.

The above summary of the present invention is not intended to describe each illustrated embodiment or every implementation of the present invention. The figures and detailed description which follow more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1A:
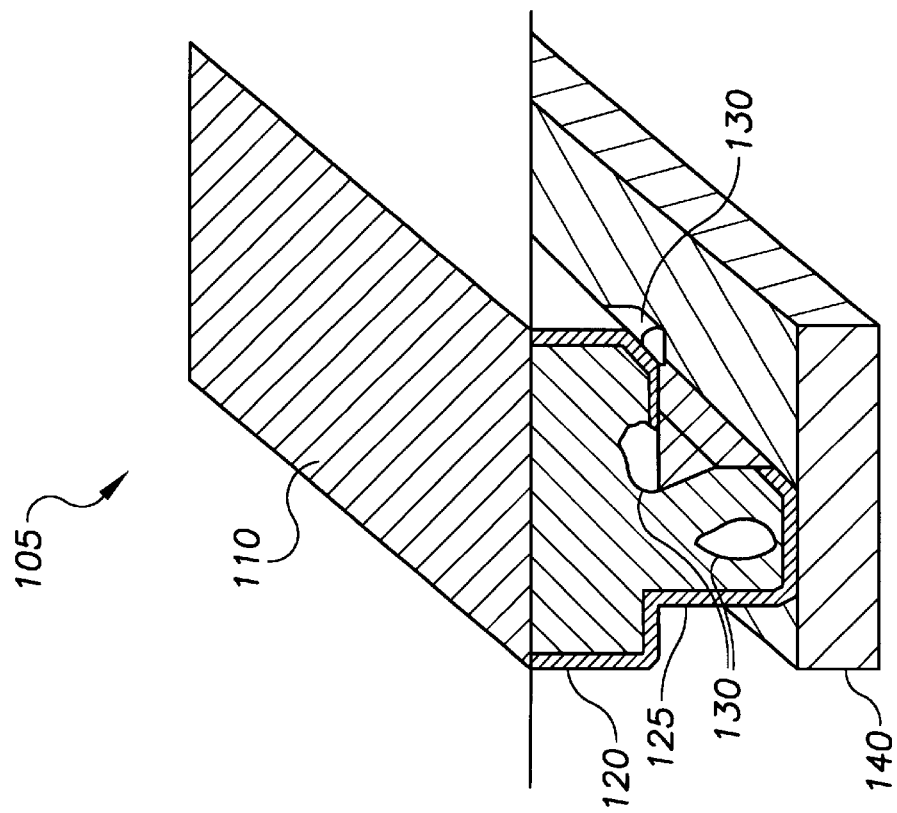
FIGS. 1A and 1B show a portion of a semiconductor device having a defect, for use in connection with an example embodiment of the present invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION

The present invention is believed to be applicable to a variety of different types of semiconductor devices, and the invention has been found to be particularly suited for devices requiring or benefiting from defect analysis of metal conductors and circuitry within the device. While the present invention is not necessarily limited to such devices, various aspects of the invention may be appreciated through a discussion of various examples using this context.

According to an example embodiment of the present invention, acoustic energy is generated in a semiconductor device having conductive structures, and acoustic waves propagate through the device. The speed of reflected and returned waves is related to the density of the material through which the waves pass. Using this speed, an index of refraction is determined, for example, via a calculation.

When a void exists in a conductive structure, the density of the region containing the void is less than a similar region not having a void. When an acoustic wave encounters a void in the conductive structure of a semiconductor device, the difference in density results in an index of refraction that is different than a similarly-obtained index from an area not having a void. The calculated index of refraction is then used to determine whether one or more voids exist in the device. Analyzing semiconductor devices for defects in this manner helps to reduce the possibility of potentially defective devices reaching an end user, and can provide an opportunity for detecting the defects early in the manufacturing process.

According to one example embodiment of the present invention, using the index of refraction to identify the existence of voids includes comparing the index of refraction from one portion of a semiconductor device to the index of refraction from another portion of the device. Depending upon the application, the portions can be randomly chosen, chosen to be in close proximity to each other, or can be specifically targeted so that a particular part of the device is analyzed.

Another manner in which to use the index of refraction to identify defects is to define a standard index of refraction for at least a portion of a non-defective semiconductor device. The standard can be determined for the device as a whole, or for target portions. Once the standard is determined from a non-defective device, an index of refraction for a portion of another semiconductor device can be detected and compared to the standard. Variation from the standard is interpreted as an indication of a defect in the device.

There are several manners in which voids are created in semiconductor devices, making the present invention useful for analyzing a variety of defects. For example, voids can be created during canal patterning, conductive film deposition, and canal and interconnect contact fill. An example process that often generates and increases the extent of such defects is Damascene processing. In one example Damascene processing technique applicable to copper, a recess or slot is created in a dielectric such as $SiO_2$. Metal is then let into the slot by blanket sputter deposition or plating onto a seed layer. The excess metal is then removed by chemical-mechanical polishing (CMP) to produce a planarized surface. The Damascene process avoids the need to delineate the metal using photoresist and substractive etching. A barrier metal is provided against the silicon and the sidewalls of the dielectric. By applying the methods described herein, processes such as Damascene processing that can generate voids are significantly improved because the voids can be detected.

Figure 1B:
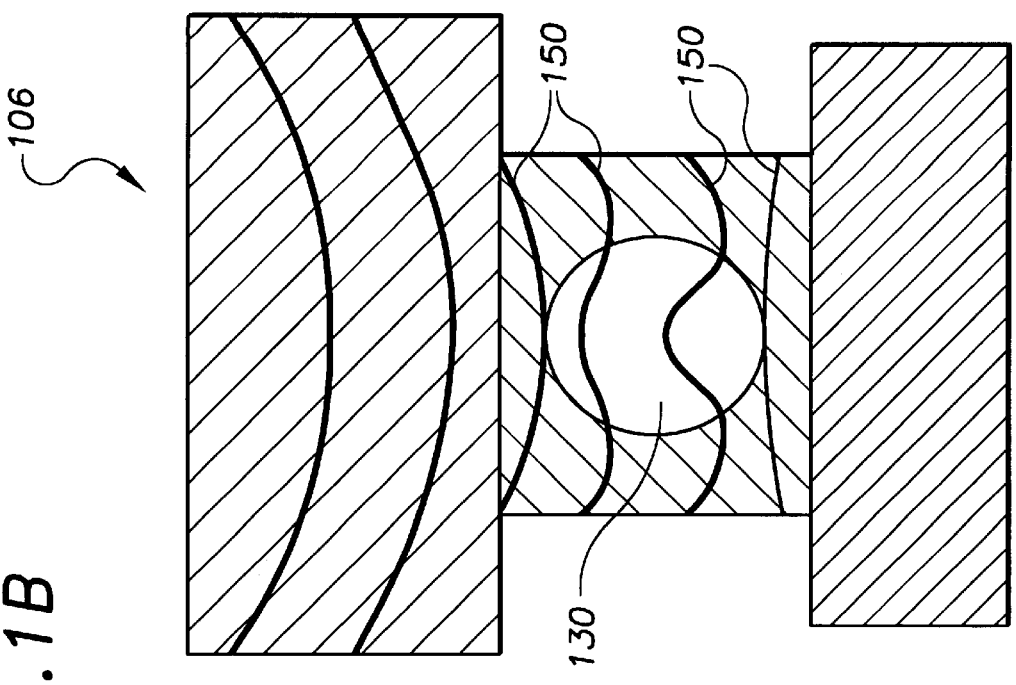

FIGS. 1A and 1B show an example defective portion of a metal conductor in a semiconductor device, according to an example embodiment of the present invention.

FIG. 1A shows voids 130 within a layer 125 of a semiconductor device 105. The layer 125 is adjacent to a metal layer 140 and a seed layer 120. Layer 110 may be, for instance, Damascene copper formed over the layer 120. FIG. 1B shows a close-up 106 of the device 105 and void 130. When acoustic waves 150 pass through the device and encounter the void 130, the waves are altered, such as shown in the void region. The altered waves can be detected and used for defect analysis.

An example method for generating acoustic energy in the semiconductor device is by using a micro-spot scanned acoustic laser. The laser is directed at the device and generates acoustic energy when the laser energy is absorbed by the material of the device, such as by the copper. The energy is absorbed as moments of thermal energy that traverse through the material as a function of the nature of the material. The acoustic energy traversing in the device is detected and an index of refraction is calculated, for example, via transducers coupled to a computer arrangement adapted to calculate the index of refraction.

Figure 2:
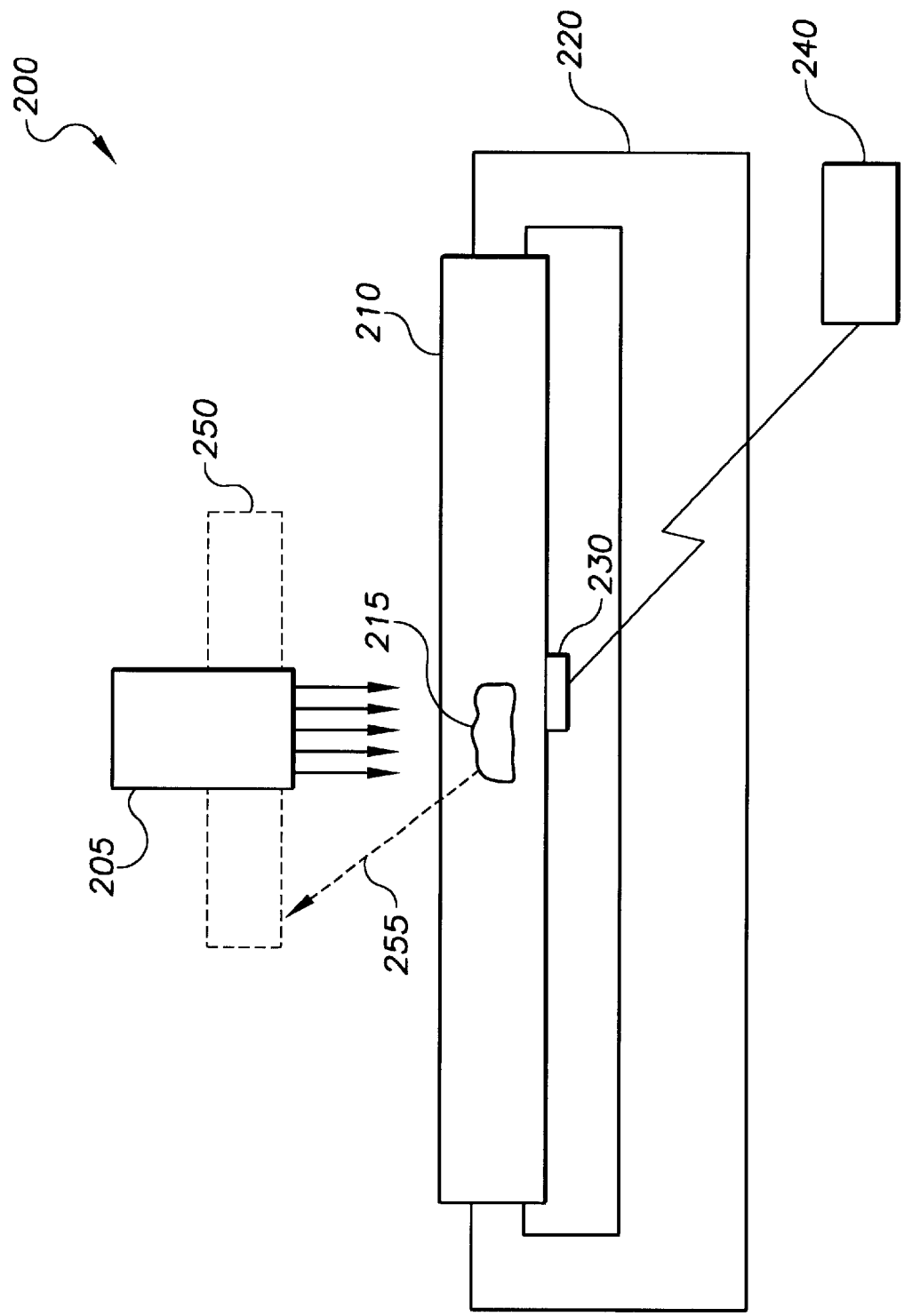
FIG. 2 shows an arrangement for analyzing a semiconductor device, according to another example embodiment of the present invention.

FIG. 2 shows a semiconductor device 200 undergoing analysis in a test arrangement 200, according to another example embodiment of the present invention. The device 210 is mounted in a fixture 220. A laser source 205 is used to direct a laser beam at a portion 215 of the device 210 and generate acoustic energy. The acoustic energy is detected at a detector 230. A computer arrangement 240 is coupled to the detector 230. The acoustic energy is used to determine an index of refraction for the portion 215 at the computer arrangement 240. The index of refraction is used and the existence of at least one defect in the portion 215 is determined.

In another example embodiment of the present invention, a photo-optic detector 250, shown in FIG. 2, is adapted to retrieve reflected waves 255 from the material. The waves may be retrieved, for instance, for periodicity and timing related to the application of the laser. When the laser is applied to the material in pulses that are very uniform in period, intensity, and timing, the response from the device can be anticipated knowing when the pulses were emitted to the material from the laser. In this manner, a standard response for a particular material can be determined and used for comparison with a device under test. Differences in the response between the standard and the device under test indicate defects in the material, such as a micro-void. Another way for making a comparison and detecting defects is to retrieve a response from two or more areas in the material via the photo-optic detector. When a defect exists in one or both of the two areas, the responses from each will be different. One manner in which to detect the difference is to subtract the responses, wherein a result that isn't about zero indicates a defect.

According to another example embodiment of the present invention, differences in the indices of refraction detected in the device using the acoustic analysis described above are indicated on a scanning map as a defect. The map can be arranged to allow the determination of the location of the defect on the device. Using this method, the location of void defects in the device can be detected, mapped, and used for analysis. In addition to determining the location of defects in a particular semiconductor device, this method can be used to characterize defects in a production lot of manufactured devices and a pattern of defects can be generated therefrom. For example, at least two semiconductor devices can be analyzed, and a scanning map can be generated for both. The maps are used and a defect pattern is developed.

As the density of metal conductors and devices within a semiconductor device increases, the possibility for the formation of voids also increases. One problem associated with the increased density stems from the formation of additional layers of metal in semiconductor devices. In accordance with a more particular example embodiment of the present invention, a semiconductor device having several layers of metal is analyzed using the acoustic analysis method described herein. Defects that exist at each level, or the lack thereof, is mapped in three-dimensions. Using such a map, defects for individual devices and defect trends for batches of devices can be analyzed.

In another example embodiment of the present invention, a portion of the semiconductor device is targeted for acoustic analysis. The targeted portion may, for instance, be located beneath one or several layers of opaque material. Acoustic energy is directed at the device and controlled to generate waves in the target portion. An example method for controlling and directing acoustic energy to a target portion is using a micro-spot scanned acoustic laser. The laser is tuned to a specific target by selecting a wavelength based on the target material. Using this method, target portions for individual or multiple devices can be analyzed, and patterns can be formed for the target portions.

Figure 3:
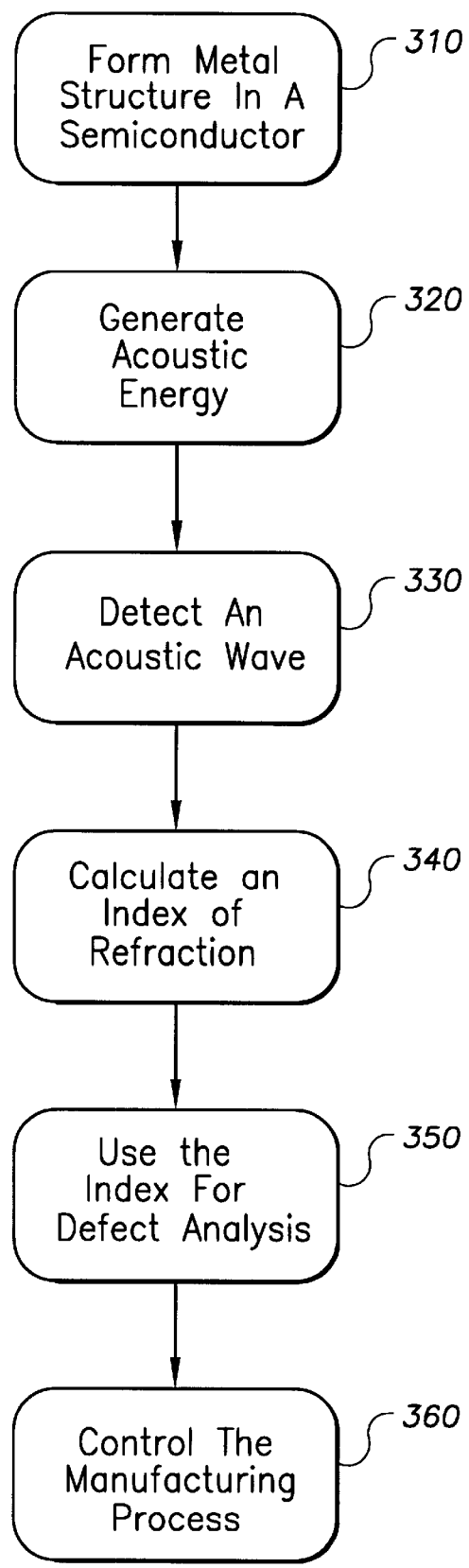
FIG. 3 is a flow chart for manufacturing a semiconductor device, according to another example embodiment of the present invention.

According to another example embodiment and referring to FIG. 3, a semiconductor device having conductive structure is manufactured. A portion of the conductive structure is formed at block 310, and acoustic energy is generated in the device at block 320. A detector is used to detect acoustic waves at block 330, and the index of refraction of a portion of the conductive structure is calculated as a function of the waves at block 340. The calculated index of refraction is used to detect at least one void at block 350 and the existence of a defect in the device is determined. In response to the index of refraction, the manufacturing process is controlled at block 360. If a defect is detected, the manufacturing process is interrupted. For example, if the defect can be corrected, the correction is made and the manufacture of the device is continued. Alternatively, the device can be discarded or, if it is determined that the defect is not significant, the manufacture of the device can be continued with the defect in existence.

Using such a method for manufacturing, the integrity of devices can be determined prior to completing their manufacture. For example, an interconnect contact could be analyzed prior to forming other structures such as a canal. In this manner, cost savings can be realized. Repairing the device and completing its manufacture preserves the effort and cost of the manufacturing steps performed prior to detection of the defect. Early detection of defects that cause the device to be nonfunctional saves the effort and cost of completing the manufacture of the device and subsequently discarding it.

While the present invention has been described with reference to several particular example embodiments, those skilled in the art will recognize that many changes may be made thereto without departing from the spirit and scope of the present invention, which is set forth in the following claims.

What is claimed is:

1. A method for analyzing a semiconductor device having conductive structure, the method comprising:
   generating acoustic energy in the device;
   detecting an acoustic wave;
   calculating an index of refraction of a portion of the conductive structure as a function of the wave; and
   using the calculated index of refraction and detecting at least one defect in the conductive structure.

2. A method for analyzing a semiconductor device, according to claim 1, wherein using the calculated index of refraction to detect at least one defect in the conductive structure comprises:
   comparing the calculated index of refraction to a standard index of refraction defined as a function of the semiconductor device and the generated acoustic energy; and
   detecting at least one defect by observing differences between the calculated and standard indices of refraction.

3. A method for analyzing a semiconductor device, according to claim 2, wherein the standard index of refraction is determined by analyzing the semiconductor device under analysis.

4. A method for analyzing a semiconductor device, according to claim 2, wherein the standard index of refraction is determined by analyzing a non-defective semiconductor device.

5. A method for analyzing a semiconductor device, according to claim 1, wherein the calculated index of refraction is relative to the density of the portion of the conductive structure.

6. A method for analyzing a semiconductor device, according to claim 5, wherein variations in density cause variations in the calculated index of refraction, and wherein the at least one defect in the conductive structure includes a metal void.

7. A method for analyzing a semiconductor device, according to claim 6, wherein the metal void results from at least one of: canal patterning, conductive film deposition, and canal fill, and interconnect contact fill.

8. A method for analyzing a semiconductor device, according to claim 1, wherein the conductive structure has undergone Damascene processing.

9. A method for analyzing a semiconductor device, according to claim 1, further comprising:
   generating a scanning map of the at least one defect; and
   using the scanning map, determining the location in the device of the at least one defect.

10. A method for analyzing a semiconductor device, according to claim 9, further comprising:
    analyzing at least one additional semiconductor device;
    generating a second scanning map of the additional device; and
    using the scanning maps, generating a defect pattern for a production lot of manufactured semiconductor devices.

11. A method for analyzing a semiconductor device, according to claim 9, wherein generating a scanning map includes generating a three-dimensional scanning map.

12. A method for analyzing a semiconductor device, according to claim 1, wherein the semiconductor device comprises a plurality of metal conductor layers, and wherein generating acoustic energy in the device includes adjusting the acoustic energy to analyze a target portion of one of the layers.

13. A method for analyzing a semiconductor device, according to claim 12, wherein the target portion includes at least one of: an interconnect contact and a canal.

14. A method for analyzing a semiconductor device, according to claim 10, wherein generating acoustic energy in the device includes adjusting the acoustic energy to analyze a target portion of each semiconductor device, and wherein generating a defect pattern includes generating a defect pattern for the target portion in each analyzed semiconductor device.

15. A method for analyzing a semiconductor device, according to claim 9, wherein the scanning map is generated for the entire device.

16. A method for analyzing a semiconductor device, according to claim 1, wherein detecting an acoustic wave comprises using a photo-optic detector arranged to retrieve reflections from material.

17. A method for manufacturing a semiconductor device comprising:
    forming conductive structure;
    generating acoustic energy in the device;
    detecting an acoustic wave;

calculating an index of refraction of a portion of the conductive structure as a function of the wave;

using the calculated index of refraction and determining whether a defect exists in the device; and responsive to detecting whether a defect exists in the device, controlling the manufacture of the device.

18. A method for manufacturing a semiconductor device, according to claim 17, wherein controlling the manufacture of the device comprises:

repairing the semiconductor device, responsive to detecting a defect; and continuing to manufacture the semiconductor device.

19. A method for manufacturing a semiconductor device, according to claim 17, wherein controlling the manufacture of the device comprises continuing to manufacture the semiconductor device, responsive to not detecting a defect.

20. A system for analyzing a semiconductor device having a conductive structure, the system comprising:

means for mounting a semiconductor device;

a laser source adapted to direct a laser beam at the device and generate acoustic energy;

means for detecting acoustic energy propagation in the device;

means for calculating an index of refraction of a portion of the conductive structure as a function of the detected acoustic energy;

means for using the calculated index of refraction and detecting at least one defect in the device.

* * * * *